United States Patent [19]

Monneret et al.

[11] Patent Number: 4,918,173

[45] Date of Patent: Apr. 17, 1990

[54] 2',6'-DIDEOXY DERIVATIVES OF ANTHRACYCLINE GLYCOSIDES

[75] Inventors: Claude Monneret, Paris; Jean-Claude Florent, Les Ulis; Agnès Genot, Villemomble, all of France

[73] Assignee: Laboratories Hoechst S.A., Puteaux, France

[21] Appl. No.: 880,075

[22] Filed: Jun. 30, 1986

[30] Foreign Application Priority Data

Jul. 2, 1985 [FR] France ............................... 85 10063

[51] Int. Cl.$^4$ ............................................. C07H 15/24
[52] U.S. Cl. ................................................... 536/6.4
[58] Field of Search ............................ 536/6.4; 514/34

[56] References Cited

U.S. PATENT DOCUMENTS 4,146,616  3/1979  Penco et al. ......................... 536/6.4
4,522,815  6/1985  Bargiotti et al. ..................... 536/6.4

Primary Examiner—Johnnie R. Brown
Assistant Examiner—Elli Peselev
Attorney, Agent, or Firm—Finnegan, Henderson, Farabow, Garrett and Dunner

[57] ABSTRACT

The present invention relates to new tetralins and their use for the preparation of anthracyclinones and anthracyclins. These tetralins contain at least one chiral carbon atom and correspond to the formula (V) below:

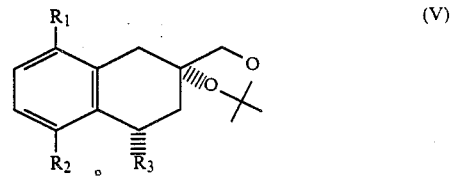

in which:
  $R_1$ and $R_2$ denote a hydrogen atom, or a halogen atom or the group $OCH_3$, provided that one of the two substituents ($R_1$ or $R_2$) must denote $OCH_3$, and
  $R_3$ denotes a hydrogen atom or the OR' group, R' being hydrogen or a hydroxyl-protecting group. Application: synthesis of glycosides of great therapeutic value.

5 Claims, No Drawings

2',6'-DIDEOXY DERIVATIVES OF ANTHRACYCLINE GLYCOSIDES

The present invention relates to new tetralins, to proeesses for their preparation, to their use for the preparation of anthracyclinones, to new glycosides (anthracyclins) obtained from these anthracyclinones, and to medications containing these glycosides.

The Applicant Company, pursuing the investigation undertaken concerning the synthesis of new glycosides of high therapeutic value (see, in particular, the Applicant Company's French Patent No. 84/03,634) has developed a new and economically very interesting process for the preparation of chiral tetralins, precursors of aglycones, which are essential for the preparation of the new anthracyclins. They can also be used to prepare (see products I to IV below) 4-demethoxydaunomycinone (III) or 4-demethoxyadriamycinone (IV), which, when coupled with daunosamine (3-amino-2,3,6-trideoxy-L-Lyxohexapyranose) yield 4-demethoxydaunorubicin and adriamycin, which are more active and less toxic than the parent compounds

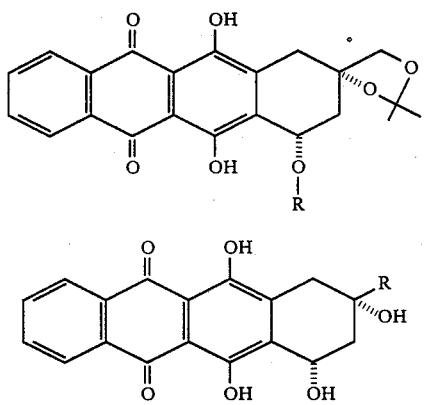

Product I: R=H
Product II: R=2-deoxy-L-fucose
Product III: R=COCH$_3$
Product IV: R=COCH$_2$OH
[see, e.g. F. Arcamone et al. Cancer Treat. Rep., 60, 829 1976].

The present invention consequently refers to tetralins containing at least one chiral carbon atom and corresponding to the formula (V) below,

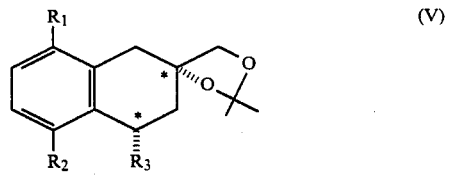

in which:
R$_1$ and R$_2$ denote a hydrogen atom or a halogen atom or the group OCH$_3$, provided that one of the two substituents (R$_1$ or R$_2$) must denote OCH$_3$, and
R$_3$ denotes a hydrogen atom or the group OR', R' being hydrogen or a hydroxyl-protecting group.

In fact, these tetralins according to the invention form key intermediates from which it is possible to derive anthracyclinones, whether natural or otherwise.

Owing to the chirality present (indicated by *) pharmacologically active anthracyclins are always finally obtained, avoiding, in contrast to the case of the other tetralins [see, for example, work by K. Tamoto et al., Chem. Pharm. Bull 32 4328 (1984)], the resolution of a racemic product, or an asymmetric synthesis, which is always difficult, or else the use of chiral auxiliaries, these processes being costly and difficult to carry out. The chiral tetralin according to the present invention avoids all these disadvantages and makes it possible to obtain, virtually certainly, pharmacologically active anthracyclins as end products.

In fact, the tetralins according to the invention provide future anthracyclins with S-configuration at carbon atom 9 and, optionally-in the case of a second chiral carbon atom-S-configuration at carbon atom 7. These two configuration are those of the natural molecules, the only ones to be active, in contrast to their enantiomers or their diastereoisomers. In addition, the presence of the isopropylidene group between the tertiary OH and the OH of the hydroxymethyl group attached to the same carbon atom S, mits simple protection of the hydroxymethyl group during the glycosidation of the hydroxy group at carbon atom 7 and preparation of 7-O-α-L-glycolsyl derivatives which are essential for obtaining a remarkable antitumor activity.

According to an advantageous embodiment of the subject of the invention, the hydroxyl-protecting group consists of tert-butyldimethylsilyl or methylethoxymethyl.

The present invention also relates to a process for preparing a tetralin according to the invention, in which an organometallic derivative of general formula (VI),

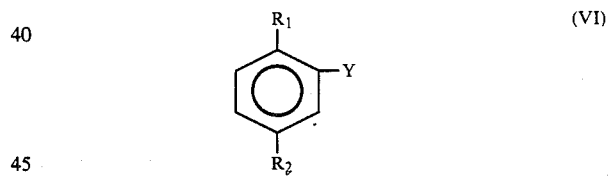

in which R$_1$ and R$_2$ have the same meaning as above, and Y=MgX or Li, X being a halogen atom, is condensed with a chiral aldehyde of general formula (VII) below,

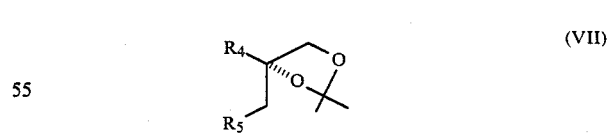

in which,
R$_4$ and R$_5$, which are always different, denote:
R$_4$ the group

or —CH$_2$OH
R$_5$ the group

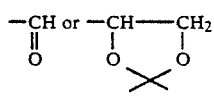

it being understood that $R_4$ or $R_5$ must denote the aldehyde group, this condensation being followed by an intramolecular cyclization.

Depending on the aldehyde chosen

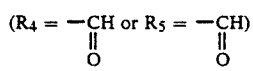

there will be two alternative ways of preparing a tetralin according to the invention.

Alternative (a):

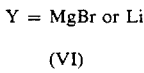

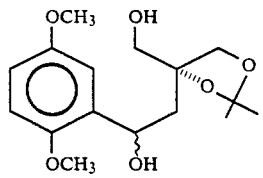

Y = MgBr or Li (VIIa)     (VI)

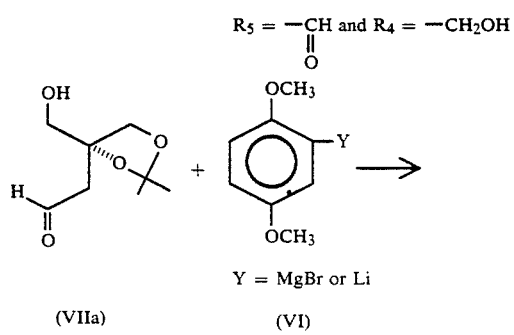

(VIII)

The aldehyde (VIIa) obtained, for example, from α-D-isosaccharino-1,4-lactone, protected beforehand in the form of an isopropylidene acetal (see French Patent No. 84/03,634) reacts with the organomagnesium or organolithium derivative of bromodimethoxybenzene (VI) and yields the adduct (VIII).

The adduct (VIII) is converted to (IX)

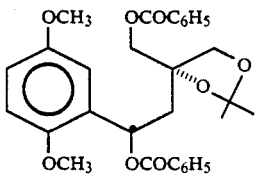

(IX)

by reaction with benzoyl chloride, and then to the alcohol (X)

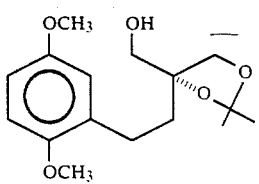

(X)

by reduction with Na metal in liquid ammonia.

The alcohol (X) is oxidized to aldehyde (XI) which, by aluminum chloride-catalyzed intramolecular cyclization, gives a mixture of tetralins (XII) and (XIII), which is converted to the required product (V) by reduction with Na in ammonia.

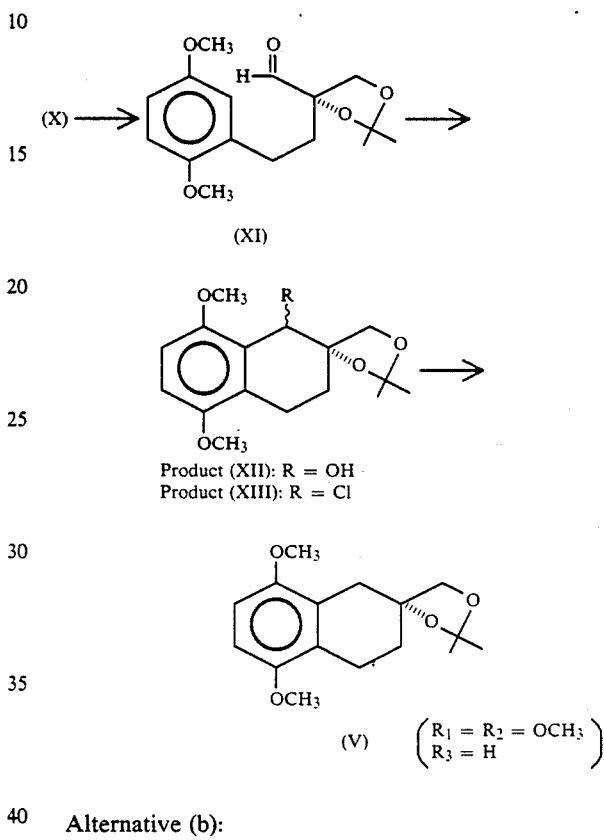

Product (XII): R = OH
Product (XIII): R = Cl (V)  $\begin{pmatrix} R_1 = R_2 = OCH_3 \\ R_3 = H \end{pmatrix}$ Alternative (b):

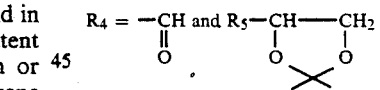

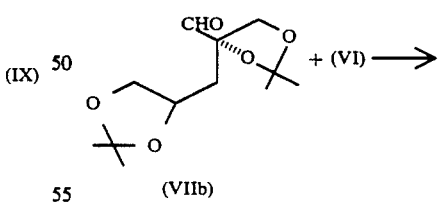

(VIIb)

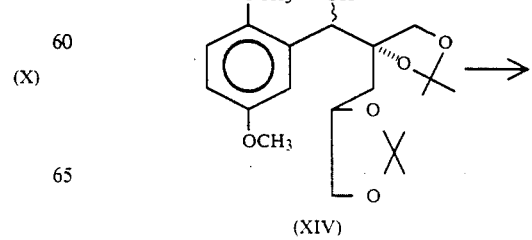

(XIV)

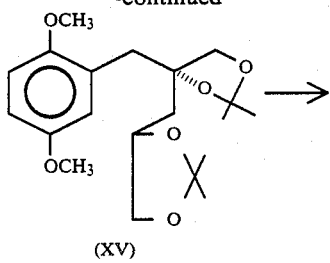

(XV)

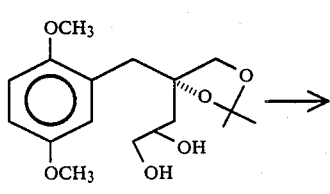

(XVI)

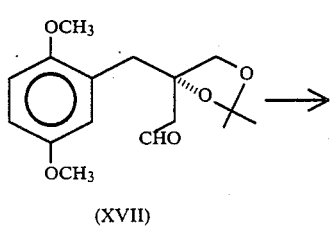

(XVII)

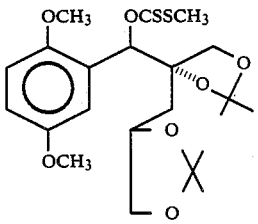

(V)

($R_1 = R_2 = OCH_3$)
($R_3 = OH$)

The aldehyde (VIIb) is condensed (at low temperature) with the organometallic derivative (VI) to give (XIV). The diastereoisomer mixture obtained is treated directly with sodium hydride, carbon disulfide and methyl iodide to form the dithiocarbonate ester (XVIII),

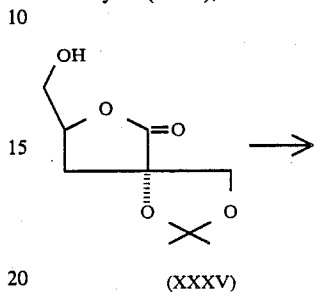 (XVIII)

Treatment of the latter with tributyltin hydride gives the deoxy derivative (XV). Selective acid hydrolysis of the terminal isopropylidene acetal of compound (XV) gives directly the glycol (XVI) precursor of the aldehyde (XVII). $SnCl_4$ treatment of (XVII) at low temperature gives, stereospecifically, the tetralin (V), which is isolated in crystalline form.

The aldehyde (VIIb) used at the starting material may be advantageously prepared by:

(a) ring opening of the lactone (XXXV) with methanol in an acid medium in the presence of α,α-dimethoxypropane,
(b) lithium aluminum hydride reduction of the bisacetonide (XXXVI) obtained, to obtain the alcohol (XXXVII), and
(c) oxidation of the latter to obtain the required aldehyde (VIIb), according to the scheme below,

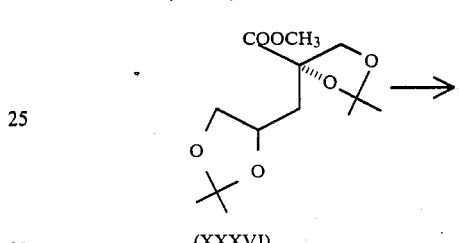

(XXXV)

(XXXVI)

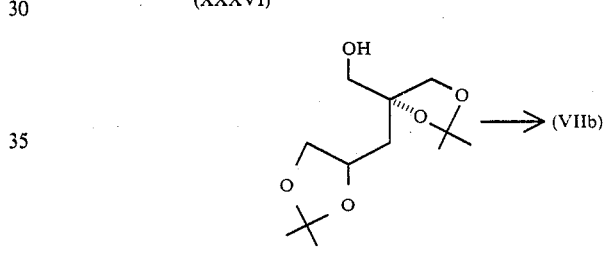

(XXXVII)

To convert the tetralins (V) according to the invention to anthracyclinones, ie. to construct the anthracyclinone framework A-B-C-D from tetralins (V) which represent the future rings A and B, several routes which are described in the literature may be employed.

It is possible, for example, to carry out, a bisacylation of the tetralin (V) by means of a modified Friedel-Crafts reaction with phthalic anhydride according to the method described, in particular, by Terashima et al. (Chem. Pharm. Bull. 31, 821 (1983));

a condensation of an anion derivative of a C-3-sulfonyl or -cyano phthalide with a monoacetalated quinone, itself derived simply and economically from the tetralin (V) [Kraus et al., Tetrahedron Letters 1978, p. 2263; or Hauser et al., JACS 99, 4533 (1977), or Swenton et al., Tetrahedron 40, 4625 and 4633 (1984), and others];

a Diels-Alder reaction between a diacetyldihydroxybenzocyclobutene and the quinone, itself derived simply and economically from the tetralin (V), according to the procedure described by Broadhurst et al., JCS, Perkin Trans., 2239 (1982).

Thus, to gain access to anthracyclinones (I)

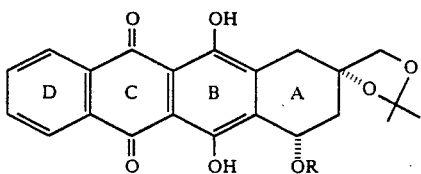
(I)

one starts either from tetralin (V) protected with a tert-butyldimethylsilyl (TBDMS) ether or from the quinone (XX) obtained by oxidation of (V) with ammonium nitrate and cerium=(V) protected or (Vb)

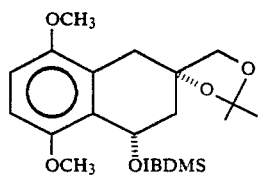

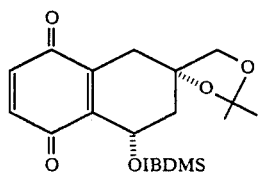
(XX)

or from the quinone monoacetal (XIX) obtained by anodic oxidation of (V), followed by selective hydrolysis,

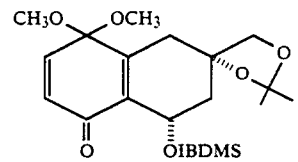
(XIX)

Coupling of the products (Vb), (XIX) and (XX) with appropriate substrates readily provides access, after removal of the protecting group, to anthracyclinone (I).

The present invention consequently relates to the glycosidation, i.e. the coupling of the aglycone (I) with various pent- or hexoses activated by the action of a halogen donor, followed by removal of protecting groups from the aglycone and then from the carbohydrate moiety. According to the invention, the pent- or hex oses taking part in the glycosidation reaction may be activated either in the form of a derivative halogenated in an anomeric position or in the form of iodonium.

According to an advantageous embodiment of the subject of the invention, the removal of protection from the aglycone is carried out by an acid hydrolysis and the removal of protection from the carbohydrate by an alkaline hydrolysis.

The operational schemes will consequently be as follows:

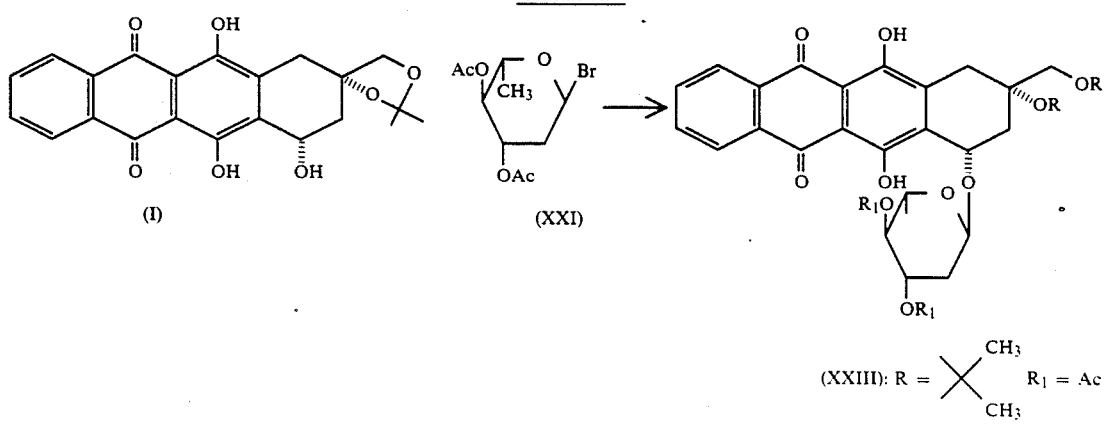

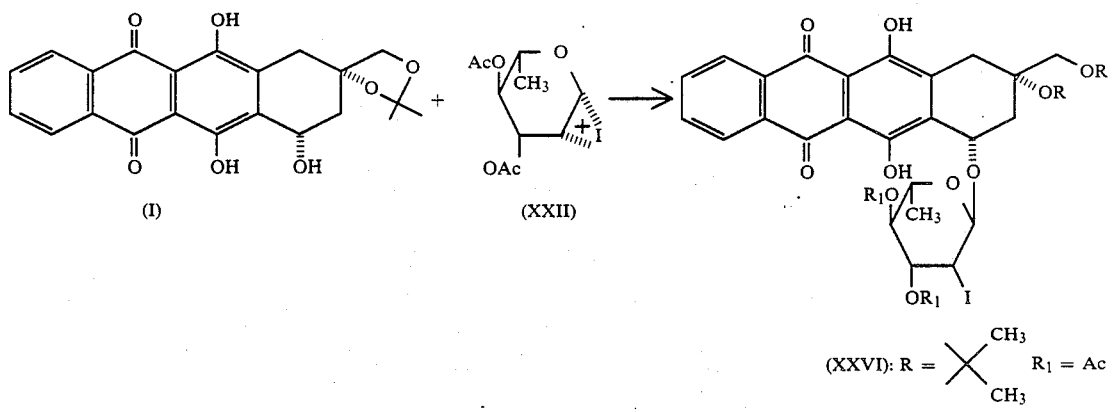

after 1st acid hydrolysis ⟶ (XXVII): R = H  R₁ = Ac after 2nd alkaline hydrolysis ⟶ (XXVIII): R = R₁ = H The glycosides (XXIII), (XXIV) and (XXV), for example, are obtained by coupling the aglycone (I) with di-O-acetyl-L-rhamnose activated in the form of the bromo derivative (XXI).

The glycosides (XXVI), (XXVII) and (XXVIII) are obtained by glycosidation of (I) with di-O-acetyl-L-rhamnose in the presence of N-iodosuccinimide. The product isolated is the glycoside (XXVI) iodine-substituted at C-2'. Removal of the protecting group from the aglycone and then from the hexose yields, respectively and successively, the iodo glycosides (XXVII) and (XXVIII).

In addition to the preceding arrangements, the invention also incorporates other arrangements which will become apparent from the following description.

The invention will be understood better with the aid of the following additional description which refers to examples of implementation of the process which is the subject of the present invention, together with a report on pharmacological experiments.

It should be clearly understood, however, that these examples of implementation and of the report on pharmacological experiments are given solely by way of illustration of the subject of the invention, and consequently do not constitute a restriction of any sort.

EXAMPLE 1

4-(2,5-Dimethoxyphenyl)-2-hydroxymethyl-2,2'-O-isopropylidene-1,2R,4R and S-butanetriol, (VIII)

first route: reaction with the organolithium derivative

A solution of butyllithium (7.3 ml; 6.2 mmol) is added dropwise to a solution of bromodimethoxybenzene (1.34 g; 6.2 mmol) in 30 ml of anhydrous THF at −78° C. under argon. The mixture is stirred for 50 minutes at this temperature.

A solution of aldehyde (VIIa) (539 mg; 3.1 mmol) in THF is then added. The mixture is stirred for 30 minutes and then a saturated solution of ammonium chloride is added and the mixture is extracted with ethyl acetate.

The organic solution is dried over sodium sulfate and concentrated under reduced pressure to give a syrup which is purified by chromatography on a silica column (solvent=2/1 hexane/acetone). 387 mg of (VIII) are obtained (yield: 40%).

second route: reaction with the organomagnesium derivative

Magnesium is activated beforehand by washing with anhydrous ether and being heated dry at 100° C. for a quarter of an hour under reduced pressure (1 mm Hg).

15 ml of a solution containing 37.5 g (172.5 mmol) of bromodimethoxybenzene dissolved in 150 ml of anhydrous ether are added, without stirring, to a three-necked flask containing 150 ml of anhydrous ether, 5.8 g (241.5 mmol) of magnesium and a crystal of iodine. The reaction is initiated by slight heating; the mixture is then stirred vigorously and the remainder of the bromodimethoxybenzene is then added over half an hour.

Stirring and refluxing are continued overnight.

The aldehyde (VIIa) (6 g; 34.5 mmol), dissolved in anhydrous ether, is then added at ambient temperature. After 6 hours, the reaction is stopped by successive addition of crushed ice, water (30 ml) and 30% strength sulfuric acid (30 ml) to dissolve magnesium hydroxide.

After extraction with ether, a syrup is obtained, which is purified as above. 677 mg of (VIII) (70%) are obtained in the form of a mixture of C-4 diastereoisomers.

$^1$H NMR (270 MHz CDCl$_3$):
7.04 (m; 1H; aromatic),
6.77 (S; 1H; aromatic),
6.71 (S; 1H; aromatic),
5.21 (q; 1H, J=4 Hz; J'=7.5 Hz; H-4 (α or β)),
5.10 (d; 1H; J=9.5 Hz; H-4 (α or β),
4.03 (d; 1H; A of AB syst.; J'=9 Hz; H-2'a),
3.92 (d; 1H; B of AB syst.; J=9 Hz; H-2'b),
3.76 (s; 3H; OMe),
3.72 (s; 3H; OMe),
3.65 (d; 1H; A of AB syst., J=11 Hz; H-1a),
3.56 (d; 1H; B of AB syst.; J=11 Hz; H-1b),
3.14 (s disap. D$_2$O; 2H; OH-1 and OH-4),
2.00 (m; 2H; H-3a and H-3b),
1.40 (s; 6H; Me of isopropylidene).

Mass spectrum (DCI/NH$_3$): m/e%: 312 (M⁺; 100); 295 (M⁺-17,88); 254 (M⁺-58, traces) 174 (5); 167 (12); 131 (40).

Analysis C$_{16}$H$_{24}$O$_6$: M=312.36

EXAMPLE 2

4-(2,5-dimethoxyphenyl-1,4-di-O-benzoate-2-O-hydroxymethyl-2,2'-O-isopropylidene-1,2R,4R and S-butanetriol, (IX)

5 ml (55 mmol) of benzoyl chloride are added to a solution of (VIII) (2.25 g; 7.21 mmol) in 20 ml of pyridine.

The mixture is left stirred at ambient temperature for 12 hours under argon.

After extraction with ether and removal of the pyridine with a 10% strength aqueous solution of sulfuric acid, (IX) is purified by column chromatography (solvent=5/1 hexane/ethyl acetate).

The product obtained (3.4 g; 94%) crystallizes from ether (M.p.: 98°-100° C.).

$^1$H NMR (400 MHz; CDCl$_3$) of the mixture of anomers [4R and 4S]

8.15 to 7.41 (m; 10H; aromatic: benzoyl groups)
7.00 to 6.79 (m; 3H; aromatic:
6.78 to 6.55 (m; 1H; H-4)
4.55 (d; 1H; A of AB syst.; J=11 Hz; H-1a)
4.49 (d; 1H; A of AB syst.; J=11 Hz; H-2'a)
4.44 (d; 1H; B of AB syst.; J=11 Hz; H-1b)
4.39 (d; 1H; B of AB syst.; J=11 Hz; H-2'b)

| | |
|---|---|
| 3.82 (s; OMe) | } 3H in all; |
| 3.81 (s; OMe) | |
| 3.75 (s; OMe) | } 3H in all |
| 3.74 (s; OMe) | |

2.64 to 2.34 (m, 2H; H-3)
1.54 (s, 3H; CH$_3$ of isopropylidene)
1.51 (s; 3H; CH$_3$ of isopropylidene)
Mass spectrum (E.I.); m/e% 520 (M+, 45); 263 (100); 205 (49); 165 (99) 122 (70); 105 (99).
Analysis: C$_{30}$H$_{32}$O$_8$ M=520.57.

EXAMPLE 3

4-(2,5-Dimethoxyphenyl)-2-hydroxymethyl-2,2'-O-isopropylidene-1,2R-butanediol, (X)

First method: reduction of the dibenzoate (IX) with Na/NH$_3$: 25 ml of ammonia are added to a solution of (IX) (250 mg; 0.48 mmol) in 5 ml of anhydrous THF at −50° C. under argon, followed by sodium until a persistent blue color is produced (approximately 60 mg). The reaction is stopped after 3 hours 30 minutes by addition of a saturated ammonium chloride solution and the mixture is extracted with ether.

92 mg of (X) (40%) are obtained.

Second method: reduction of the sodium salt with Na/NH$_3$: 300 mg (0.96 mmol) of (VIII) are dissolved in 5 ml of anhydrous THF cooled to 0° C. 62 mg (2.11 mmol) of 80% sodium hydride are added in small portions. After 1 hour to 0° C. the mixture was cooled to −50° C. and 50 ml of liquid ammonia were then added, followed by sodium until a persistent blue color is produced.

The reaction is stopped in the same manner as before by addition of a saturated ammonium chloride solution and the mixture is extracted with ether.

After purification by flash chromatography (2/1 hexane/ethyl acetate) to remove the unreacted diol, 110 mg (i.e. a yield of 40%) of alcohol (X), which is in the form of a syrup, are obtained.

$[\alpha]_D^{20}$ = +5° (c=1.2; CHCl$_3$).
$^1$H NMR (270 MHz, CDCl$_3$)
6.80 to 6.50 ppm (m; 3H; aromatic)
3.92 (d; 1H; A of AB syst.; J=9 Hz; H-2'a)
3.81 (d; 1H; B of AB syst.; J=9 Hz; H-2'b)
3.75 (s; 3H; OMe)
3.73 (s; 3H; OMe)
3.62 (d; 1H; A of AB syst.; J=11 Hz; H-1a)
3.60 (s, disap. D$_2$O; 1H; OH)
3.54 (d; 1H; B of AB syst.; J=11 Hz; H-1b)
2.72 to 2.48 (m; 2H; H-4a; H-4b)
2.02 to 1.77 (m; 2H; H-3a; H-3b)
1.44 (s; 3H; Me of isopropylidene)
1.43 (s; 3H; Me of isopropylidene)

EXAMPLE 4

4-(2,5-Dimethoxyphenyl)-2(S)hydroxy-2-hydroxymethyl-2,2'-0-isopropylidenebutanal, (XI)

750 mg (2.5 mmol) of alcohol (X) are dissolved in 70 ml of dichloromethane. 2.4 g of activated 3 Å molecular sieve and 1.9 g (5.05 mmol) of pyridinium dichromate are added.

After 3 hours ether (100 ml) is added and the reaction mixture is filtered on Celite. After concentration 400 mg (55%) of (XI) are obtained in this manner.

$[\alpha]_D^{20}$ = −4° (c=2.2; CHCl$_3$)
$^1$H NMR (270 MHz; CDCl$_3$)
9.60 (s; 1H; aldehyde)
6.75 to 6.62 (m; 3H; aromatics)
4.20 (d; 1H; A of AB syst.; J=9 Hz; H-2'a)
3.80 (d; 1H; B of AB syst.; J=9 Hz; H-2'b)
3.74 (s; 3H; OMe)
3.72 (s; 3H; OMe)
2.72 (sext; 1H; A of ABXY syst.; J=12.5 Hz; J'Δ12.5 Hz; J''=5 Hz; H-4a)
2.51 (sext; 1H; B of ABXY syst.; J=12.5 Hz; J'=12 Hz; J''=5 Hz; H-4b)
2.07 (sext; 1H; X of ABXY syst.; J=12.5 Hz; J'=5 Hz; J''=12 Hz; H-3a)
1.92 (m; 1H; Y of ABXY syst.; J=12.5 Hz; J'=5 Hz; J''=12 Hz; H-3b)
1.47 (s; 3H; Me of isopropylidene)
1.43 (s; 3H; Me of isopropylidene)
Mass spectrum (IE) m/e% 294 (M+; 35); 279 (M+.−15, traces); 265 (M+.−29, 9); 207 (37); 151 (100).
Analysis: C$_{16}$H$_{22}$O$_5$, M=294.34.

EXAMPLE 5

1,2R-Dihydroxy-2-hydroxymethyl-2,2'-0-isopropylidene-5,8-dimethoxy-1,2,3,4-tetrahydronaphthalene and 1-chloro-2S-hydroxy-2-hydroxymethyl-2,2'-0-isopropylidene-5,8-dimethoxy-1,2,3,4-tetrahydronaphthalene, (XII) and (XIII)

95 mg of aluminum chloride (0.7 mmol) are added in small portions to a solution of aldehyde (XI) (200 mg; 0.7 mmol) in dichloromethane (10 ml) at a temperature of −78° C. After 1 hour's stirring the reaction mixture is poured onto a mixture of crushed ice and aqueous sodium bicarbonate.

After extraction with dichloromethane and chromatography on a silica column (solvent=95/5 toluene/ethyl acetate) 50 mg of a mixture of (XII) and (XIII) and 70 mg of the starting material are obtained. A second chromatography on silica enables (XIII) to be isolated:

$^1$H NMR (270 MHz; CDCl$_3$)

6.67 (d; 1H; J=9 Hz; aromatic),
6.62 (d; 1H; J=9 Hz; aromatic),
5.11 (d; 1H; H-1),
4.23 (d; 1H; A of AB syst.; J=9 Hz; H-2'a),
3.96 (d; 1H; B of AB syst.; J=9 Hz; H-2'b),
3.80 (s; 3H; OMe)
3.73 (s; 3H; OMe)
2.94 (dd; 1H; A of ABXY syst.; J=19 Hz; J'=7 Hz; H-4a),
2.74 (octet; 1H; B of ABXY syst.; J=19 Hz; J'=12 Hz; J''=7 Hz; H-4b),
2.33 (octet; 1H; X of ABXY syst.; J=13 Hz; J'=12 Hz; J''=7 Hz; H-3a),
1.93 (dd; 1H; Y of ABXY syst.; J=13 Hz; J'=7 HZ; H-3b)
1.41 (s; 3H; Me of isopropylidene)
1.36 (s; 3H; Me of isopropylidene).
Mass spectrum (IE) m/e%. 312 (M+, 48%); 297 (M+−15, 7), 237 (7), 219 (30), 198 (26), 177 (51), 43 (100).

EXAMPLE 6

2R-Hydroxy-2-hydroxymethyl-2,2'-0-isopropylidene-5,8-dimethoxy-1,2,3,4-tetrahydronaphthalene, (V) ($R_1=R_2=OCH_3$; $R_3=H$)

The mixture of (XII) and (XIII) (50 mg) is dissolved in anhydrous THF (3 ml) and then 15 ml of ammonia are added in small quantities at −60° C., followed by sodium until a persistent blue color is obtained. The mixture is left to react for 1 hour 30 minutes. After addition of 1 ml of a saturated ammonium chloride solution and evaporation of the ammonia the residue is extracted with ether.

A product showing a spot which is less polar than (XII) and (XIII) is obtained (solvent: 2/1 hexane/ethyl acetate). After chromatography on a silica column (1/1 hexane/dichloromethane) 30 mg of (V) ($R_1=R_2=OCH_3$ and $R_3=H$) are obtained in the form of a syrup $[\alpha]_d^{20} = +1°$ (c=0.7; CHCl$_3$)

$^1$H NMR (270 MHz; CDCl$_3$)
6.55 (s; 2H; aromatics)
3.81 (d; 1H; A of AB syst.; J=9 Hz; H-2'a)
3.80 (d; 1H; B of AB syst.; J=9 Hz; H-2'b)
3.74 (s; 6H; OMe)
2.87 (m; 1H; A of ABXY syst.; J=17 Hz; J'=7 Hz; J''=6 Hz; H-4a)
2.86 (d; 1H; A of AB syst.; J=15 Hz; H-1a)
2.75 (d; 1H; B of AB syst.; J=15 Hz; H-1b)
2.66 (m; 1H; B of ABXY syst.; J=17 Hz; J'=7 Hz; J''=6 Hz; H-4b)
2.01 (m; 1H; X of ABXY syst.; J=13 Hz; J'=7 Hz; J''=6 Hz; H-3a)
1.78 (m; 1H; Y of ABXY syst.; J=13 Hz; J'=7 Hz; J''=6 Hz; H-3b)
1.43 (s; 6H; Me of isopropylidene).
Analysis $C_{16}H_{22}O_4$, M=278.34.

EXAMPLE 7

Methyl 2S,4S,5-trihydroxy-2-hydroxymethyl-2,2':4,5-di-0-isopropylidenepentanoate, (XXXVI)

α,α-Dimethoxypropane (120 ml) and 5 g of Amberlyst 15 resin are added to a solution of lactone (XXXV) (15 g; 92 mmol) in methanol (30 ml). After 75 hours' stirring at ambient temperature the reaction mixture is filtered on Celite and evaporated to dryness.

After column chromatography (solvent: hexane followed by 4/1 hexane/acetone), 19.5 g (77%) of (XXXVI) are obtained in the form of a syrup.
$[\alpha]^{20} = -17°$ (c 2; CHCl$_3$),
IR; γmax (film): 1750 (c=O); 1220 cm$^1$ (C—O),
$^1$H NMR (270 MHz; CDCl$_3$),
4.25 (d; 1H; A of AB syst.; J=9 Hz; H-2'a),
4.16 (m; 1H; H-4),
4.10 (dd; 1H; A of ABX syst.; J=8 Hz; J'=6.6; Hz; H-5a),
3.85 (d; 1H; B of AB syst.; J=9 Hz; H-2'b),
3.74 (s; 3H; COOMe),
3.54 (dd; 1H; B of ABX syst.; J=8 Hz; J'=7 Hz; H-5b)
2.27 (dd; 1H, A of ABX syst.; J=13 Hz; J'=7 Hz; H-3a)
1.87 (dd; 1H; B of ABX syst.; J=13 Hz; J'=5 Hz; H-3b)
1.43 (s; 6H) and 1.34 (s; 3H); 1.30 (s; 3H)=Me isopropylidenes.
Analysis: $C_{13}H_{22}O_6$, M=274.28.

EXAMPLE 8

3-Deoxy-2R-C-hydroxymethyl-2,2':4,5-di-0-isopropylidene-D-glyceropentitol, (XXXVII)

Lithium aluminum hydride (2.8 g; 73 mmol) is added in small portions to a solution of ester (XXXVI) (19 g; 69 mmol) in anhydrous ether (300 ml). After reaction overnight at reflux, the reaction is stopped by successive addition of 2.8 ml of water followed by 2.8 ml of 15% strength aqueous sodium hydroxide, and, finally, 8.4 ml of water.

After filtration on a layer of Celite and evaporation, 16.5 g (97%) of (XXXVII) are obtained.
$[\alpha]_D^{20} = -10°$ (C 1, CHCl$_3$),
$^1$H NMR (270 MHz; CDCl$_3$),
4.32 (m, 1H; H-4), 4.10 (dd; 1H; J=8.5 Hz; J'=6 Hz and 3.49 (t, 1H, J'=8 Hz) ABX syst.; H-5),
4.01 (d, 1H) and 3.75 (d, 1H) (AB syst.; J=9 Hz; H-2')
3.63 (d, 1H) and 3.57 (d, 1H) (AB syst.; J=12 Hz; H-1)
1.87 (m, 2H; H-3); 1.37 (s, 6H); 1.36 (s, 3H) and 1.35 (s; 3H)=Me of isopropylidenes.
Analysis $C_{12}H_{22}O_5$, M=246.30.

EXAMPLE 9

1-(2,5-Dimethoxyphenyl)-1R and S,2R, 4S,5-tetrahydroxy-3-deoxy-2-hydroxymethyl-2,2':4,5-di-0-isopropylidenepentitol, (XIV)

53 ml of butyllithium (59.4 mmol) are added to a solution of bromodimethoxybenzene (12.9 g, 59.4 mmol) in anhydrous THF (300 ml) at a temperature of −78° C.

After 1 hours' stirring at this temperature, the aldehyde (VIIb) (12.1 g; 49.5 mmol) is added slowly as a solution in THF (50 ml).

After 1 hour's stirring the reaction is stopped by controlled addition of a saturated solution of ammonium chloride. After extraction with ether a syrup is obtained which is chromatographed on a silica column (solvent: 20/1, then 10/1 hexane/acetone). 12 g (63%) of (XIV) are obtained.

$^1$H NMR (270 MHz; CCDCl$_3$)
7.08 (s; 1H; aromatic)
6.71 (s; 2H; aromatics)
5.18 (s; 1H; H-1)
4.32 (m; 1H; H-4)

4.23 (d; 1H; A of AB syst.; J=8.5 Hz; H-2'a)
3.97 (dd; 1H; A of ABX syst.; J=8 Hz; J'=6 Hz; H-5a)
3.74 (s; 3H; OMe)
3.72 (s; 3H; OMe)
3.69 (d; 1H; B of AB syst.; J=8.5 Hz; H-2'b)
3.40 (dd; 1H; B of ABX syst.; J=8 Hz; J'=8 Hz; H-5b)
2.09 (dd; 1H; A of ABX syst.; J=15 Hz; J'=7 HZ; H-3a),
1.66 (dd; B of ABX syst.; J=15 Hz; J'=4.5 Hz; H-3b)
1.40 (s; 6H; Me of isopropylidene),
1.34 (s; 3H; Me of isopropylidene),
1.30 (s; 3H; Me of isopropylidene),
Mass spectrum (I.E.) m/e%,
382 (M+.; traces); 367 (M+.−15; traces); 249 (6); 215 (57); 167 (14); 166 (22); 157 (18); 101 (100).
Analysis: $C_{20}H_{30}O_7$; M=382.41.

EXAMPLE 10

1-(2,5-dimethoxyphenyl)-3-deoxy-1(R) and (S), 2(S), 4(S), 5-tetrahydroxy-1-0-methyldithiocarbonate-2-hydroxymethyl-2,2'-4,5-0-isopropylidene pentitol Sodium hydride (641 mg; 1.5 equivalents) is added at 0° C. to a solution of alcohol (XIV) (6.8 g; 17.8 mmol) in anhydrous THF (150 ml).

After 30 minutes, carbon disulfide (3.2 ml; 53.4 mmol) is added dropwise, followed after 1 hour 30 minutes' stirring at 0° C., by methyl iodide (5 ml; 80 mmol). The mixture is allowed to warm up to ambient temperature (overnight) and is evaporated to dryness. The residue obtained is chromatographed on a silica column (solvent: 5/1 hexane/ethyl acetate) (6.5 g; 77%). I.R. ν max (film): 1220 cm$^{-1}$ (C=S).

EXAMPLE 11

1-(2,5-Dimethoxyphenyl)-1,3-dideoxy-2-C-hydroxymethyl-2,2';4,5-di-0-isopropylidene-D-ribitol (XV)

4 ml (15 mmol) of tributyltin hydride and 100 mg of azaisobutyronitrile are added to 4.5 g (9.5 mmol) of (XVIII) dissolved in 300 ml of toluene.

The mixture is heated at reflux under argon for 2 hours.

The cold reaction mixture is filtered and then concentrated. The product obtained is chromatographed on a silica column (solvent=hexane, followed by an increasing proportion of dichloromethane).

3 g (86%) of (XV) are obtained.
$[\alpha]_D^{20}=+5°$ (c=2.4; CHCl$_3$),
$^1$H NMR (270 MHz; CDCl$_3$),
6.8 (s; 1H; aromatic),
6.7 (s; 2H; aromatics),
4.34 (m, 1H; H-4),
4.05 (dd, 1H, A of ABX syst.; J=8 Hz; J'=5.5 Hz; H-5a),
3.82 (d; 1H; A of AB syst.; J=9 Hz; H-2'a)
3.74 (d; 1H; B of AB syst.; J=9 Hz; H-2'b),
3.73 (s; 3H; OMe),
3.72 (s; 3H; OMe),
3.44 (dd; 1H; B of ABX syst.; J=8 Hz; J'=8 Hz; H-5b)
2.98 (s; 2H; H-1),
1.89 (dd; 1H; A of ABX syst.; J=13.5 Hz; J'=6.5 Hz; H-3a),
1.77 (dd; 1H; B of ABX syst.; J=13.5 Hz; J'=5.5 Hz; H-3b),
1.39 (s; 3H) 1.36 (s; 6H) and,
1.17 (s; 3H; Me of isopropylidene)
Analysis $C_{20}H_{30}O_6$; M=366.45.

EXAMPLE 12

1-(2,5-Dimethoxyphenyl)-1,3-di-deoxy-2-C-hydroxymethyl-2,2'-0-isopropylidene-D-ribitol, (XVI)

6 g of (XV) (16.4 mmol) are dissolved in a water-methanol mixture (4:1; 100 ml) to which 3 drops of 12N HCL are added. After 6 hours' reaction, the mixture is neutralized by addition of Amberlite resin IR 45 (OH$^-$).

After concentration a syrup is obtained which is chromatographed on a silica column (eluent=1/1 hexane/dichloromethane followed by pure dichloromethane). 2.3 g of (XVI) and 2 g of (XV) are obtained and treated again; thus, in two operations, 3 g of (XVI) (56%) are obtained.

$[\alpha]_D^{20}=+13°$ (c=2.4; CHCl$_3$),
$^1$H NMR (270 MHz; CDCl$_3$),
6.86 (m; 1H; aromatic),
6.60 (m; 2H; aromatics),
3.98 (m; 1H; H-4)
3.94 (d; 1H; A of AB syst.; J=9 Hz; H-2'a),
3.80 (d; 1H; B of AB syst.; J=9 Hz; H-2'b),
3.75 (s; 3H; OMe),
3.74 (s; 3H; OMe),
3.50 (dd; 1H; A of ABX syst.; J=11 Hz; J'=3 Hz; H-5a),
3.37 (dd; 1H; B of ABX syst.; J=11 Hz; J'=7 Hz; H-5b),
3.30 (broad s, disap. D$_2$O; 1H; OH),
3.03 (d; 1H; A of AB syst.; J=14 Hz; H-1a),
2.91 (d; 1H; B of AB syst.; J=14 Hz; H-1b),
2.44 (broad s, disap. D$_2$O; 1H; OH)
1.79 (dd; 1H; A of ABX syst.; J=15 Hz; J'=9 Hz; H-3a),
1.56 (dd; 1H; B of ABX syst.; J=15 Hz; J'=3 Hz; H-3b),
1.40 (s; 3H),
1.32 (s; 3H); (Me of isopropylidenes)
Analysis $C_{17}H_{26}O_6$ M=326.38.

EXAMPLE 13

4-(2,5-Dimethoxyphenyl)-3S-hydroxy-3-hydroxymethyl-3,3'-0-isopropylidene-butanal (XVII)

2.28 g of (XVI) (7 mmol) are dissolved in aqueous methanol (1/1=30 ml). 1.65 g of sodium metaperiodate (7.7 mmol) in solution in 2 ml of water are added. After 1 hour and 30 minutes the reaction mixture is filtered and then extracted with dichloromethane. 2 g of (XVII) (97%) are obtained as a syrup.

$[\alpha]_D^{20}=+4°$ (c=3.2; CHCl$_3$) IR νmax (film)=2820 and 2720 (aldehyde); 1720 (C=0)
$^1$H NMR (270 MHz; CDCl$_3$)
9.66 (d; 1H; J=2 Hz; aldehyde)
6.77 (s; 1H; aromatic)
6.69 (s; 2H; aromatic)
4.00 (d; 1H; A of AB syst.; J=9 Hz; H-3a)
3.82 (d; 1H; B of AB syst.; J=9 Hz; H-3b)
3.73 (s; 3H; Ome)
3.70 (s; 3H; OMe)
3.03 (d; 1H; A of AB syst.; J=14 Hz; H-4a)
2.94 (d; 1H; B of AB syst.; J=14 Hz; H-4b)
2.64 (dd; 1H; A of ABX syst.; J=18 Hz; J'=2 Hz; H-2a), 2.48 (dd; 1H; B of ABX syst., J=18 Hz; J'=2 Hz; H-2b),
1.37 (s; 3H) and,
1.35 (s; 3H) (Me of isopropylidenes).
Analysis: $C_{16}H_{22}O_5$, M=294.34.

EXAMPLE 14

1S,3S-Dihydroxy-3,3'-O-isopropylidene-3-hydroxymethyl-5,8-dimethoxy-1,2,3,4-tetrahydronaphthalene (V) ($R_1=R_2=OCH_3$ and $R_3=OH$)

$SnCl_4$ (700 mg, 2.72 mmol) is added to a solution of aldehyde (XVII) (800 mg, 2.72 mmol) in anhydrous dichloromethane (30 ml) at a temperature of −78° C. After 2 h 30 min of reaction the reaction is stopped by addition of triethylamine (2 ml) and then, after evaporation of the reaction mixture under reduced pressure, the residue is diluted with dichloromethane and washed with water. After concentration, 670 mg of comopound (V) ($R_1=R_2=OCH_3$ and $R_3=OH$) (83%) are obtained, showing a single spot in TLC (solvent: 1/1 hexane/acetone), and crystallizing from a hexane/acetone mixture.

M.p. 148° C. (hexane/acetone)
$[\alpha]_D^{20}=+31°$ (c=0.73, $CHCl_3$),
$^1H$ NMR (270 MHz; $CDCl_3$),
6.64 (s, 2H, H-aromatics),
5.06 (m, 1H, J=9; J'=6; J''=4 Hz, H-1),
4.16 (d, 1H, disap. $D_2O$; J=9 Hz, OH),
3.85 (s, 2H, H-3'),
3.78 (s, 3H, $OCH_3$),
3.72 (s, 3H, $OCH_3$),
3.03 (d, 1H, A of AB syst., J=18 Hz, H-4a),
2.66 (d, 1H, B of AB syst., J=18 Hz, H-4b),
2.35 (dd, 1H, J=14 HZ, J'=4 HZ, H-2a),
1.98 (dd, 1H, J=14 Hz, J'=6 Hz, H-2b),
1.43 (s, 3H) and 1.36 (S, 3H),
Mass spectrum (DCI/$NH_3$) m/e% 312 ($M+NH_4^+$ traces); 295 ($M+H^+$, 18); 294 ($M^+$, 100); 277 ($M+H^+$-18,33).
Analysis: $C_{16}H_{22}O_5$, M=294.34.

EXAMPLE 15

1S-tert-Butyldimethylsilyloxy-1,2,3,4-tetrahydro-3S-hydroxy-3-hydroxymethyl-3,3'-O-isopropylidene-5,8-dimethoxynaphthalene (Vb)

Imidazole (2.03 g, 13.5 mmol), followed by tert-butyldimethylsilyl chloride (1.9 g, 27 mmol) are added to a solution of tetralin V (790 mg, 2.7 mmol) in anhydrous DMF (20 ml). After one night at 100° C. under argon, the reaction mixture is cooled and then extracted with ether. The organic phase is washed with water and then dried over sodium sulfate and concentrated under reduced pressure. After removal of excess reactant by chromatography on a light layer of silica, 960 mg (87%) of protected Vb are isolated and crystallized from hexane:

M.p. 59° C. $[\alpha]_D^{20}=+30°$ (c=1; $CHCl_3$)
$^1H$ NMR (270 MHz; $CDCl_3$),
6.76–6.62 (m, 2H, aromatics);
5.21 (t, 1H, H-1, J=J'=6 Hz),
3.76 (s, 6H, 2 OMe),
3.67 (s, 2H, H-3),
3.06 (d, 1H, A of AB syst., H-4a),
2.95 (d, 1H, B of AB syst., J=16 Hz, H-4b),
2.25 (d, 2H, H-2, J=6 Hz),
1.51 and 1.46 (2s, 3H, isopropylidene $CH_3$)
0.91 (s, 3H, $CH_3$)
0.20 and 0.08 (2s, 3H, 2 $CH_3$)

M.s. (DCI/$NH_3$): m/e 294 ($M+H^+$-115, 100%); 277 (32),
201 (7), 92 (9)

EXAMPLE 16

1S-tert-Butyldimethylsilyloxy-1,2,3,4,5,8-hexahydro-3S-hydroxy-3-hydroxymethyl-3,3'-O-isopropylidene-5,5-dimethoxynaphthalene-8-one (XIX)

A solution of Vb (500 mg, i.e. 1.22 mmol) in 1% strength methanolic potassium hydroxide (100 ml) is oxidized anodically (cell with a platinum electrode thermostated at 0° C. and placed under a potential of 1.3 V). The reaction is monitored using the UV spectrum until the peak at 290 nm has disappeared. A TLC (2/1 hexane/acetone) shows the appearance of a product which is slightly more polar than Vb. The mixture is evaporated to dryness and extracted with ether. In this way 590 mg of a yellow oil are obtained, showing two spots in TLC (see above): a mixture of bis and monoketal.

The mixture is converted completely to a monoketal by treating the residue for 5 minutes at ambient temperature with acetone (5 ml) containing 2.5 ml of 10% strength aqueous acetic acid. The solution is then neutralized with sodium hydrogen carbonate and then extracted with ether. 470 mg of monoketal 19 are obtained (90% yield) in the form of a yellow syrupy residue: $[\alpha]_D^{20}=+16°$ (c=1, $CHCl_3$).

$^1H$ NMR (270 MHz, $CDCl_3$),
6.72 (d, 1H, J=10, H-7),
6.38 (d, 1H, J=10, H-6),
4.84 (m, 1H, H-1),
3.74 (m, 2H, H-3),
3.30 and 3.25 (2s, 3H, 2 OMe),
2.57 (m, 2H, H-4),
1.47 and 1.43 (2s, 3H, isopropylidene Me),
0.90 (s, 9H, 3 $CH_3$),
0.22 and 0.17 (2s, 3H, 2 $CH_3$).

EXAMPLE 17

1-O-(3',4'-Di-O-acetyl-2',6'-dideoxy-α-L-arabinohexopyranosyl)-1,2,3,4,6,11-hexahydro-1S,3S,5,12-tetrahydroxy-3-hydroxymethyl-3,13-O-isopropylidenenaphthacene-6,11-dione (XXIII)

A stream of HBr is passed through a solution of di-O-acetyl-L-rhamnal (200 mg, 0.93 mmol) in anhydrous benzene (25 ml) for approximately 10 min, and the solution is then evaporated to dryness under reduced pressure. The residue is taken up twice with approximately 5 ml of benzene and reevaporated to dryness. The aglycone 1 (75 mg, 0.19 mmol) dissolved in anhydrous dichloromethane (25 ml) is then added, followed by yellow mercury oxide (610 mg), mercuric bromide (210 mg) and 3 Å molecular sieve (900 mg). After 18 hours' stirring at ambient temperature, the reaction mixture is filtered and the filtrate is concentrated under reduced pressure. A flash chromatography on silica with elution with a 10/1 and then a 4/1 hexane/ethyl acetate mixture enables 75 mg of pure (XXIII) to be isolated (yield 65%), with $R_f$ of 0.23 (4/1 hex./EtOAc) or 0.45 (9/1 tol./acetone) or 0.82 (2/1 hex./acetone). One recrystallization from a hexane/acetone mixture gives: m.p. 235°–236° C.;
$[\alpha]_D^{20}=+148°$ (c=0.04, $CHCl_3$);
I.R. $\nu_{max}^{CHCl_3}$ 1740, 1225 and 1040 (ester CO) and 1625 and 1590 $cm^{-1}$ (chelated quinone).
$^1H$ NMR (270 MHz, $CDCl_3$), 13.70 (1H, s) and 13.44 (1H, s) (2 chelated phenol OH)
8.25 (2H, m) and 7.86 (2H, m) AA' and BB' syst., 4H, aromat.).

5.50 (1H, broad. s: $J_{WE}$ 7 Hz, H-1),
5.26 (1H, m, H-3'),
5.04 (1H, t, J=J'=4 Hz, H-1'), 4.77 (1H, t, J=J'=10 Hz, H-4'),
4.20 (1h, m, J=6.5, J'=10 Hz, H-5'),
3.90 (2H, s, A$_2$, CH$_2$-13),
3.24 (1H, d) and 2.90 (1H, d) (AB syst., J=17.5, CH$_2$-4)
2.03 (3H, s) and 1.98 (3H, s) (2 OAc)
1.26 (3H, d, J=6.5, CH$_3$-6')

M.s. (DCI/NH$_3$): m/e%: 628 (15), 414 (10), 396 (28), 381 (15), 338 (3), 321 (32), 250 (1100), 232 (30), 215 (35), 190 (20), 172 (17), 155 (65), 95 (40).

Analysis: C$_{32}$H$_{34}$O$_{12}$, M=610.59.

EXAMPLE 18

1-O-(3',4'-Di-O-acetyl-2',6'-dideoxy-α-L-arabinohexopyranosyl)-1,2,3,4,6,11-hexahydro-1S,3S,5,12-tetrahydroxy-3-hydroxymethylnaphthacene-6,11-dione (XXIV)

A solution of (XXIII) (50 mg, 0.081 mmol) in 0.2N methanolic hydrogen chloride (25 ml) is stirred at room temperature. The reaction is followed by TLC (2/1 hexane/acetone) and shows the gradual appearance of a more polar product (R$_f$ 0.67). After 4 h the reaction mixture is poured into a saturated solution of sodium hydrogen carbonate and is then extracted with dichloromethane. A conventional extraction enables 45 mg of crude product to be isolated. A flash chromatography with elution with a 2/1 hexane/acetone mixture gives, in order of elution, 14 mg of starting material (XXIII), followed by 7 mg of pure crystalline (XXIV). A sample is recrystallized for analysis: m.p. 216°-217° C.;

$[\alpha]_D^{20}$ +110° (c=0.04, CHCl$_3$);
I.R. $_{max}^{CHCl_3}$ 3550 (OH), 1730, 1225 (ester CO) and 1625 and 1590 cm$^{-1}$ (chelated quinone);
$^1$H NMR (270 MHz, CDCl$_3$),
13.70 (1H, s) and 13.44 (1H, s) (2, chelated phenol OH),
8.35 (2H, m) and 7.92 (2H, m) (AA' and BB' syst., 4H aromat.)
5.54 (1H, broadened s, $J_{wH}$~7-8 Hz, H-1)
5.28 (1H, broadened s, $J_{wH}$~8 Hz, H-1')
5.10 (1H, m, H-3')
4.84 (1H, t, J=J'=10 Hz, H-4')
4.13 (1H, m, J=6.5, J'=10 Hz, H-5')
3.79 (1H, d) and 3.56 (1H, d) (AB syst., J=11, CH$_2$-13)
3.30 (1H, d) and 2.66 (1H, d) (AB syst., J=18.5 Hz, CH$_2$-4)
2.04 (3H, s) and 1.96 (3H s) (2 OAc)
1.25 (3H, d, CH$_3$-6')

EXAMPLE 19

1-O-(2',6'-dideoxy-α-L-arabinohexopyranosyl)-1,2,3,4,6,11-hexahydro-1S,3S,5,12-tetrahydroxy-3-hydroxymethylnaphthacene-6,11-dione (XXV)

Sodium methoxide (0.08 ml) is added to a solution of (XXIV) (8 mg) in absolute methanol (3 ml) and the solution is stirred at 0° C. until the TLC (2/1 hexane/acetone) shows the total disappearance of (XXIV) (R$_f$ 0.67) and the appearance of a more polar product (R$_f$ 0.20). The pH of the violet-colored solution is then adjusted to ≃6 by gradual careful addition of 1M HCl. Evaporation under reduced pressure leaves a residue (7 mg) which is chromatographed on silica H. Elution with a 95/5 dichloromethane/methanol mixture yields 5 mg of pure (XXV). M.s. (DCI/NH$_3$): m/e% 504 (M$^+$NH$_4^+$, 100); 497 (M+H$^+$, 28) 468 (M-18,10), 451(7) 374(27), 356(59), 338(7), 321(7), 148(43).

EXAMPLE 20

1-O-(3',4'-Di-O-acetyl-2',6'-dideoxy-2'-iodo-α-L-mannopyranosyl)-1,2,3,4,6,11-hexahydro-1S,3S,5,12-tetrahydroxy-3-hydroxymethyl-3,13-O-isopropylidenenaphthacene-6,11-dione (XXVI)

Di-O-acetyl-L-rhamnal (300 mg, 1.4 mmol) is added to a solution of aglycone 1 (80 mg, 0.2 mmol) in acetonitrile (5 ml), followed by N-iodosuccinimide dissolved in ether (340 mg, 1.5 mmol in 5 ml). The mixture is left stirred for 18 h in the absence of light, and is then diluted with dichloromethane. The organic solution is washed with a solution of sodium thiosulfate (the color disappears) and then with water and is concentrated under reduced pressure. The residue is taken up with methanol (7 ml) and water (3 ml) in the presence of crushed ice. The precipitate which forms is separated off and then dried. In this way 60 mg of crude product which contains only the glycosides are isolated. Chromatography of this product on silica (95/5 toluene/acetone) makes it possible to isolate 40 mg of pure α L glycoside crystallizing from methanol: m.p. 155°-160°; $[\alpha]_D^{20}$=+29° (c=0.15, CHCl$_3$).

I.R. $\nu_{max}^{CHCl_3}$ 3500(OH), 1740, 1225 (ester CO) and 1625 and 1590 cm$^{-1}$ (chelated quinone)
$^1$H NMR (270 MHz, CDCl$_3$),
13.55 (1H, s) and 13.27 (1H, s) (2 chelated phenol OH)
8.28 (2H, m) and 7.77 (2H, m) (AA' and BB' syst., 4H aromat.),
5.75 (1H, s, H-1'),
5.13 (1H, dd, J=J'=10 Hz, H-4'),
5.01 (1H, broadened s, $J_{WH}$~12 Hz, H-1),
4.66-4.48 (2H, m, H-2' and 3'),
4.28 (1H, m, H-5'),
3.96 (1H, d) and 3.88 (1H, d) (AB syst., J=18, CH$_2$-13)
3.28 (1H, d) and 2.86 (1H, d) (AB syst., J=12.5 Hz, CH$_2$-4), 2.42-1.79 (2H, m, CH$_2$-2),
2.02 L (3H, s) and 2.01 (3H, s) (2 OAc),
1.48 (3H, s) and 1.46 (3H, s) (Me of isopropylidene),
1.25 (3H, d), J=6.5 Hz, CH$_3$-6'),
M.s. (DCI/NH$_3$) m/e%: 754 (M+NH$_4^+$, 100), 737 (M+H$^+$, traces), 716 (14), 628 (10), 414 (4), 396 (17), 376 (12), 358 (2), 341 (8).

EXAMPLE 21

1-O-(3',4'-Di-O-acetyl-2',6'-dideoxy-2'-iodo-α-L-mannopyranosyl)-1,2,3,4,6,11-hexahydro-1S,3S,5,12-tetrahydroxy-3-hydroxymethylnaphthacene-6,11-dione (XXVII)

A solution of (XXVI) (40 mg) in a mixture of 6 ml of acetic acid, 2 ml of methanol and 2 ml of water is heated at 50° C. for 18 hours. After cooling and neutralization with sodium bicarbonate, the reaction mixture is extracted with dichloromethane. After solvent evaporation 35 mg of crude product are obtained. The latter is chromatographed on silica (eluent: 1/1 hexane/acetone).

M.p. 235°: $[\alpha]_D$=+141° (c=0.06, CHCl$_3$): I.R. 3500 (OH), 1625 and 1590 cm$^{-1}$ (chelated quinone).

R$_f$ 0.55 (1/1 hexane/acetone) and 0.18 (2/1).

¹H NMR (270 MHz, CDCl₃).

13.56 (1H, s) and 13.30 (1H, s) (2 chelated phenolic OH)

8.25 (2H, m) and 7.75 (2H, m) (AA' and BB' syst., 4H aromat.)

5.75 (1H, S, H-1'), 5.25 (1H, broadened s, H-1), 5.21 (1H, dd, J=J'=10 Hz, H-4'), 4.63 (1H, dd, J=4.5; J'=1, H-2'), 4.33 (1H, dd, J=10; J'=4.5, H-3'), 4.13 (1H, m, H-5'), 3.95 (1H, broadened s, disappearing on deuteration, OH), 3.70 (1H, d) and 3.50 (1H, d) (AB syst., j=10, CH₂-13), 3.21 (1H, d) and 2.59 (1H, d) (AB, J=18.5, CH₂-4), 2.05 (3H, s) and 2.03 (3H, s) 2 OAc), 1.32 (3H, d, CH₃-6'), 2.53 (1H, d, J=13, H-2e) and 1.83 (1H, dd, J'-3.5, H-2a).

M.s. (DCI/NH₃): 714 (M+NH+), 697 (M+H+), 356 (aglycone), 321 (aromatized aglycone).

EXAMPLE 22

1-O-(2',6'-Dideoxy-2'-iodo-α-L-mannopyranosyl)-1,2,3,4,6,11-hexahydro-1S,3S,5,12-tetrahydroxy-3-hydroxymethylnaphthacene-6,11-dione (XXVIII)

This compound is obtained from XXVII under the conditions for the preparation of XXV. It is purified by chromatography on silica H with elution with pure acetone. It is obtained in a crystalline state:

M.p. 218°–219° C.; [α]$_D^{20}$=+32° (c=0.038, methanol)

PHARMACOLOGICAL REPORT

Effect on L 1210 leukemia cells

A. Operating procedure:

The test is carried out in accordance with the method of Hamburger and Salmon, modified as follows:

The medium employed is replaced by that of Mc Coy 5 A. The number of cells placed in the dishes is reduced to 5 10²/dish on account of the rapid growth of the L 1210 leukemia cells.

The cells are incubated for 1 hour at 37° C. in the presence of various concentrations of the tested substance. The cells are then washed twice with Mc Coy 5 A and placed on agarose plates according to the method of Hamburger and Salmon.

Furthermore, the test is carried out in parallel with continuous incubation with various concentrations of the substance under study by introducing the substance into the agarose layer before the cells are left to incubate. The dishes are placed in the oven at 37° C. under an atmosphere of 5% CO₂ and 20% O₂, and a relative humidity of 95% for 5 to 7 days. After this time the colonies with a diameter greater than 60 mcm are counted with the aid of a reversed microscope.

B. The results:

The results summarized in Table I below are expressed as a percentage of the colonies produced with treated L 1210 cells compared to the untreated controls. When the experiments are repeated, the variation coefficient is less than 15%.

Two experiments are carried out, one with 1 hour's exposure, the other with continuous exposure.

| No | Formulae | IC 50 in μg/ml 1 h exposure | Continuous exposure |
|---|---|---|---|
| XXIII | | 2.8 | >10 |
| XXIII after de-esterification of the oside | | >1 | >1 |
| XXIV | | 0.021 | 3.6 |

| No | Formulae | IC 50 in μg/ml 1 h exposure | Continuous exposure |
|---|---|---|---|
| XXV | 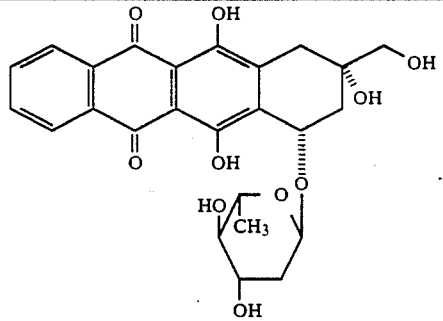 | 0.025 | 0.063 |
| DOXORUBICIN | | | |

The daily dosage in man is of the order of 1 to 2 mg/kg, expressed as active substance.

As follows from the above, the invention is in no way restricted to those of its methods of use, of implementation and of application which have just been described in a more explicit manner; on the contrary, it includes all the alternative forms which may occur to the expert in this field, without departing from the limits nor from the scope of the present invention.

We claim:

1. An anthracyclin consisting of 1-O-(3',4'-di-O-acetyl-2',6'-dideoxy-α-L-arabinohexopyranosyl)-1,2,3,4,6,11-hexahydro-1S,3S,5,12-tetrahydroxy-3-hydroxymethyl-3,13-O-isopropylidenenaphthacene-6,11-dione of formula (XXIII) below:

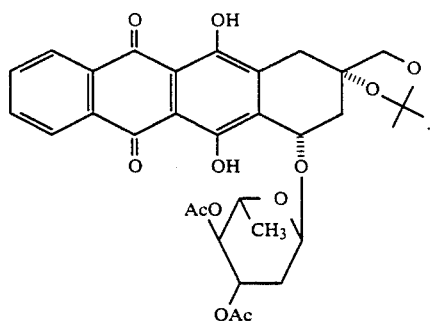

2. The anthracyclin consisting of 1-O-(3',4'-di-O-acetyl-2',6'-dideoxy-α-L-arabinohexopyranosyl)-1,2,3,4,6,11-hexahydro-1S,3S,5,12-tetrahydroxy-3-hydroxymethylnaphthacene-6,11-dione of formula (XXIV) below:

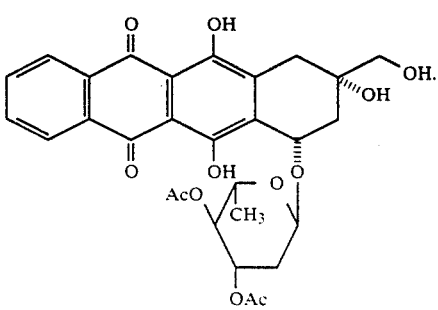

3. The anthracyclin consisting of 1-O-(2',6'-dideoxy-α-L-arabinohexopyranosyl)-1,2,3,4,6,11-hexahydro-1S,3S,5,12-tetrahydroxy-3-hydroxymethyl, of formula (XXV), below:

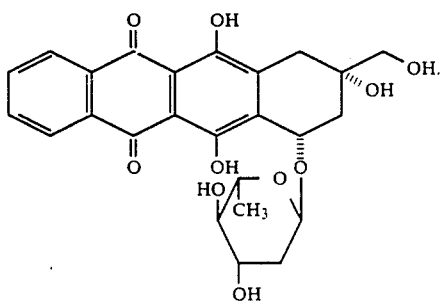

4. The anthracyclin consisting of 1-O-(3',4'-di-O-acetyl-2',6'-dideoxy-2'-iodo-α-L-mannopyranosyl)-1,2,3,4,6,11-hexahydro-1S,3S,5,12-tetrahydroxy-3-hydroxymethylnaphthacene-6,11-dione of formula (XXVII) below:

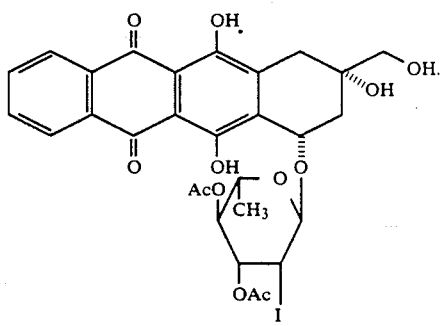

5. The anthracyclin consisting of 1-(2',6'-dideoxy-2'-iodo-α-L-mannopyranosyl)-1,2,3,4,6,11-hexahydro-1s,3s,5,12-tetrahydroxy-3-hydroxymethylnaphthacene-6,11-dione of formula (XXVIII) below:

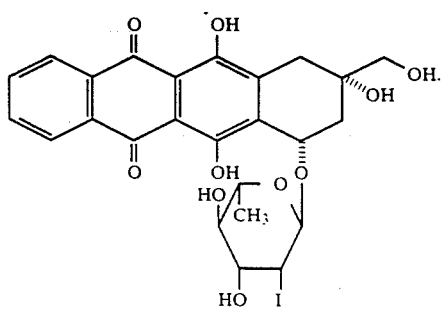

* * * * *

UNITED STATES PATENT AND TRADEMARK OFFICE
CERTIFICATE OF CORRECTION

PATENT NO. : 4,918,173
DATED : April 17, 1990
INVENTOR(S) : Claude Monneret et al It is certified that error appears in the above-identified patent and that said Letters Patent is hereby corrected as shown below:

Columns 23-24, last line of Table I, "DOXORUBICON" should be followed by --0.02-- and --0.04-- in the first and second columns, respectively.

Claim 3, column 24, first line should read --1S,3S,5,12-tetrahydroxy-3-hydroxymethyl, of formula--.

Claim 5, column 24, line 54, replace "1s,3s" with --1S,3S--.

Signed and Sealed this

Thirtieth Day of July, 1991

Attest:

HARRY F. MANBECK, JR.

*Attesting Officer*     *Commissioner of Patents and Trademarks*